US00PP09849P

United States Patent [19]

Meilland

[11] Patent Number: Plant 9,849

[45] Date of Patent: Apr. 8, 1997

[54] FLORIBUNDA ROSE PLANT NAMED 'MEINIPS'

[75] Inventor: Alain A. Meilland, Antibes, France

[73] Assignee: The Conard-Pyle Company, West Grove, Pa.

[21] Appl. No.: 544,391

[22] Filed: Oct. 17, 1995

[51] Int. Cl.[6] ..... A01H 5/00

[52] U.S. Cl. ..... Plt./22

[58] Field of Search ..... Plt./22, 26, 25

*Primary Examiner*—Howard J. Locker

*Attorney, Agent, or Firm*—Burns, Doane, Swecker & Mathis, L.L.P.

[57] ABSTRACT

A new and distinct variety of Floribunda rose plant is provided which abundantly forms attractive pastel pink blossoms that exhibit a light fragrance. The plant exhibits a bushy growth habit. Attractive very dense medium green and glossy vegetation is formed. The new variety is particularly well suited for growing as ornamentation in the landscape.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) was the 'Deltep' variety (non-patented in the United States). The male parent (i.e., the pollen parent) of the new variety was the product of the cross of the 'Meilena' variety (non-patented in the United States) and the 'Rumba' variety (U.S. Plant Pat. No. 1,919). The 'Meilena' variety sometimes is known as the 'Poppy Flash' variety. The parentage of the new variety can be summarized as follows:

'Deltep'×('Meilena'×'Rumba').

The seeds resulting from the above pollination were sown and 22 small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive pastel pink blossoms,
(b) exhibits a bushy growth habit,
(c) exhibits a light fragrance,
(d) forms attractive very dense medium green and glossy vegetation, and
(e) is particularly well suited for growing as ornamentation in the landscape.

The new variety has undergone asexual propagation by a number of routes in France, including budding, grafting, and cuttage. The characteristics of the new variety have been found to be strictly transmissible by such asexual propagation from one generation to another in France.

The new variety has been named the 'Meinips' variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during May while growing on their own roots outdoors at Le Cannet des Maures, Var, France.

DETAILED DESCRIPTION

Figures 1, 2, 3, 4, 5, 6, 7, 8, 9, 10, 11, 12, 13, 14, 15, 16:
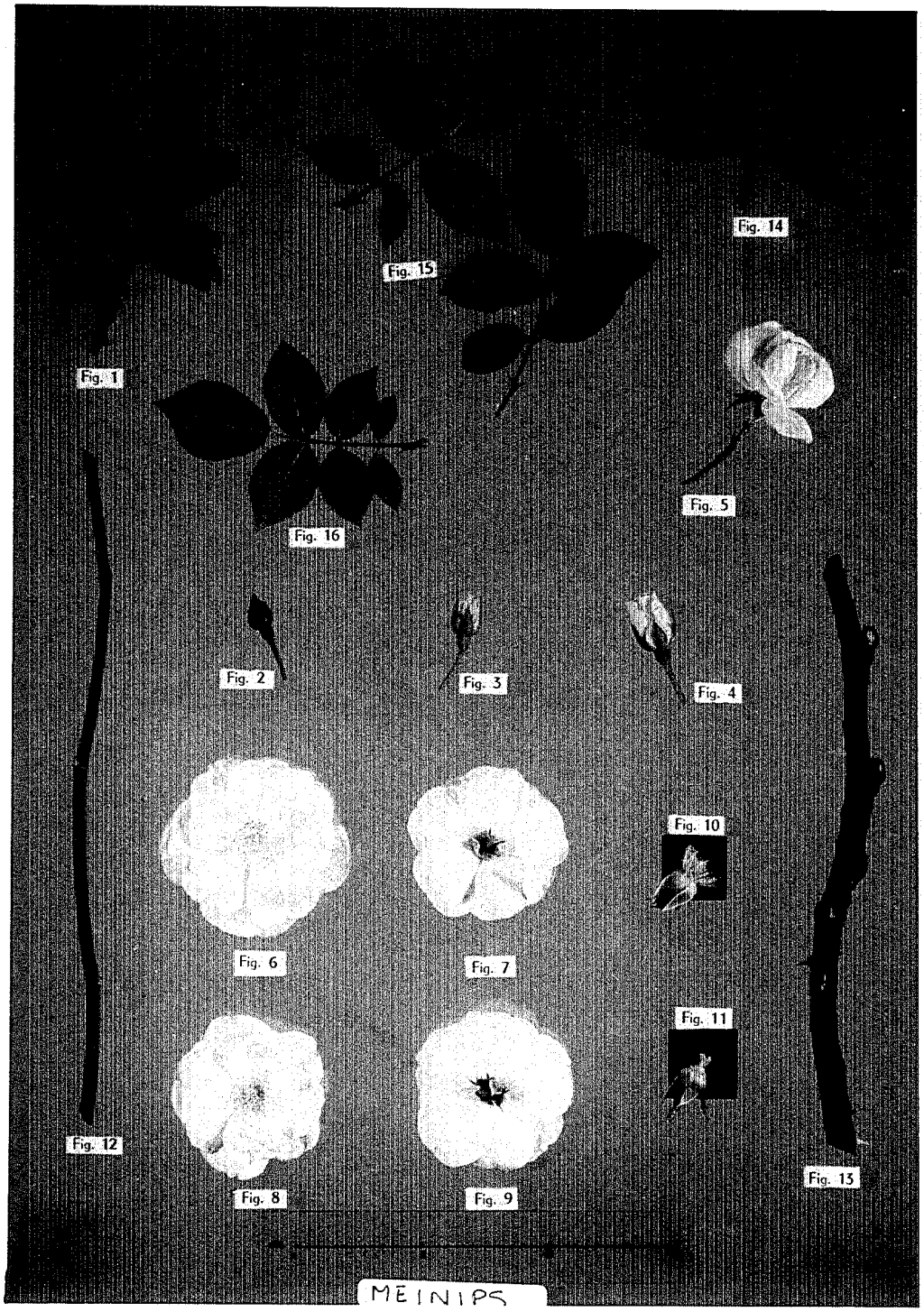
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — upper surface.
FIG. 15 illustrates specimens of two leaves with five leaflets — upper surface (right) and under surface (left)
FIG. 16 illustrates a specimen of a leaf with seven leaflets — under surface.

The chart used in the identification of the colors is that of The Royal Horticultural Society (R.H.S. Colour Chart). The terminology which precedes reference to the chart has been added to indicate the corresponding color in more common terms. The description is based on two year old specimens of the new variety during May while growing on their own roots at LeCannet des Maures, Var, France.

Class: Floribunda.

Plant:

*Height.*—Plants commonly achieve a height of approximately 100 to 110 cm. at the end of the growing season.

*Habit.*—Bushy.

Branches:

*Color.*—Young stems: reddish brown. Adult wood: Yellow-Green Group 146C.

Thorns.—Size: medium. Quantity: generally absent on young stems and infrequent on mature wood (as illustrated). Color: greenish-tan on mature wood (as illustrated).

Leaves:

*Stipules.*—Adnate, pectinate, wide and relatively large.

*Petioles.*—Upper surface: striped reddish on young foliage and light green, Yellow-Green Group 147C, on adult foliage and widely suffused with Greyed-Red Group 178A. Under surface: medium green, Yellow-Green Group 146D and suffused with reddish coloration.

*Leaflets.*—Number: 3, 5, and 7. Shape: elliptic. Serration: single and regular. Texture: consistent. General appearance: very dense, glossy, and medium green. Color (young foliage): Upper surface: Yellow-Green Group 148A suffused with reddish coloration. Under surface: Yellow-Green Group 148A suffused with reddish coloration. Color (adult foliage): Upper surface: Yellow-Green Group 146A. Under surface: light green, Yellow-Green Group 146B.

Inflorescence:

*Number of flowers.*—Commonly approxiately 6 to 15 flowers per stem.

*Peduncle.*—Medium green suffused with reddish coloration, commonly with some prickles, more or less glandular, and approximately 5 cm. in length on average.

*Sepals.*—Upper surface: tomentose, and greenish in coloration. Under surface: greenish suffused with reddish coloration, and with apendiculate edges.

*Buds.*—Shape: conical and of a somewhat distinctive configuration (as illustrated). Length: approximately 2 to 3 cm. on average. Size: medium. Color upon opening: Upper surface: Vermilion, Red Group 41B at the margins; Mandarin Red, Red Group 41D at the middle; and Buttercup Yellow, Yellow Group 15A at the base. Under surface: Vermilion, Red Group 41B at the margins; Mandarin Red, Red Group 41D at the middle; and Buttercup Yellow, Yellow Group 15A at the base.

*Flower.*—Shape: cup-shaped with a high center. Diameter: approximately 7 cm. on average. Color (when opening begins): Upper surface: Azalea Pink, Red Group 41C at the margins; light orange, Orange Group 28D at the middle; and Buttercup Yellow, Yellow-Orange Group 15B at the base. Under surface: Azalea Pink, Red Group 41C at the margins; orange, Orange Group 29B at the middle; and Buttercup Yellow, Yellow-Orange Group 15B at the base. Color (when blooming): Upper surface: Azalea Pink, Red Group 41C at the margins; light orange, Orange Group 28D at the middle; and Buttercup Yellow, Yellow-Orange Group 15B at the base. Under surface: Azalea Pink, Red Group 41C at the margins; orange, Orange Group 29B at the middle; and Buttercup Yellow, Yellow-Orange Group 15B at the base. Color (at end of opening): Upper surface: Geranium Red, Red Group 47D at the margins; light Carmine Pink, Red Group 52D at the middle; and Buttercup Yellow, Yellow-Orange Group 15A at the base. Under surface: Claret Rose, Red Group 50B at the margins; light Claret Rose, Red Group 50C at the middle; and Buttercup Yellow, Yellow-Orange Group 15B at the base. Fragrance: light. Petal drop: good. Petal form: rounded. Petal number: approximately 18 on average and commonly with approximately 6 petaloids on average. Stamen number: approximately 70 to 80 on average. Anthers: ochre in coloration. Filaments: ochre in coloration. Pistils: approximately 60 on average. Stigmas: ochre in coloration. Styles: yellowish in coloration. Receptacle: light green and widely suffused with reddish brown in coloration, and in longitudinal section in the shape of a pear.

Development:

*Vegetation.*—Strong.

*Blooming.*—Abundant.

*Aptitude to bear fruit.*—Good.

*Resistance to diseases.*—Very good with resistance to Marssonina disease.

I claim:

1. A new and distinct variety of Floribunda rose plant characterized by the following combination of characteristics:

(a) forms in abundance attractive pastel pink blossoms,
(b) exhibits a bushy growth habit,
(c) exhibits a light fragrance,
(d) forms attractive very dense medium green and glossy vegetation, and
(e) is particularly well suited for growing as ornamentation in the landscape;

substantially as herein shown and described.

* * * * *

MEINIPS